United States Patent [19]

Allen

[11] 4,009,717
[45] Mar. 1, 1977

[54] RETAINING FLUIDS

[76] Inventor: Clayton H. Allen, 651 Concord Ave., Cambridge, Mass. 02138

[22] Filed: June 27, 1975

[21] Appl. No.: 590,810

[52] U.S. Cl. ............................................. 128/294
[51] Int. Cl.² ......................................... A61F 5/42
[58] Field of Search .......... 128/294, 295, 138, 157, 128/407, 408, 412

[56] References Cited

UNITED STATES PATENTS

| 2,410,460 | 11/1946 | Robinson | 128/294 |
| 2,839,060 | 6/1958 | Ormo | 128/294 |

FOREIGN PATENTS OR APPLICATIONS

| 593,637 | 11/1930 | Germany | 128/294 |
| 326,719 | 6/1929 | United Kingdom | 128/294 |

Primary Examiner—Robert W. Michell
Assistant Examiner—Henry S. Layton
Attorney, Agent, or Firm—Charles Hieken; Jerry Cohen

[57] ABSTRACT

A condom comprises inner and outer sheaths with the region between the inner and outer sheaths forming a fluid reservoir so that the inside of the inner sheath remains dry.

12 Claims, 14 Drawing Figures

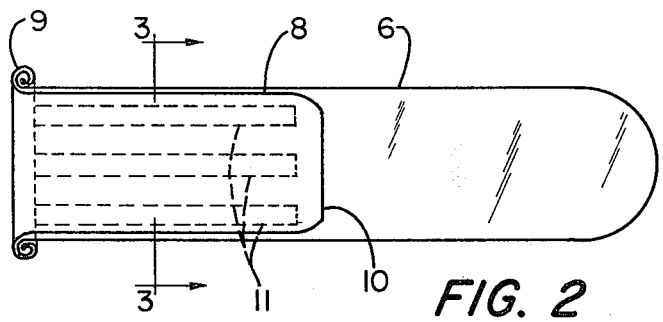
FIG. 2
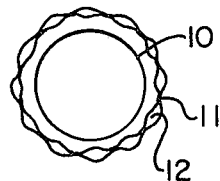
FIG. 3
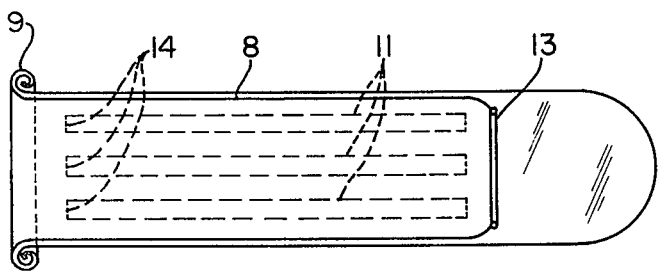
FIG. 4
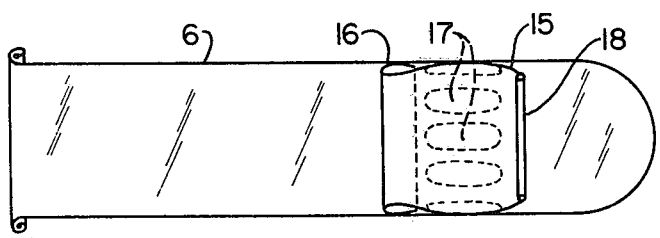
FIG. 5
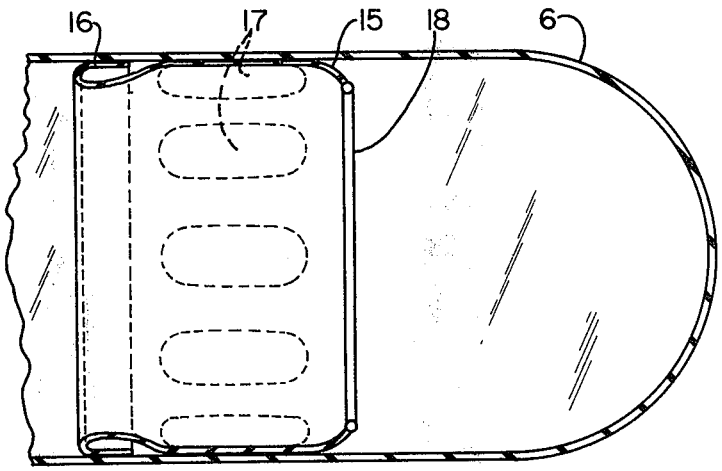
FIG. 6
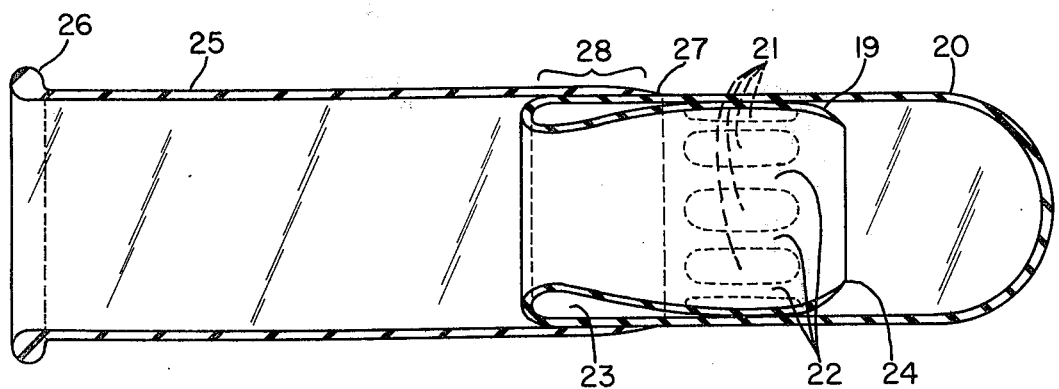

RETAINING FLUIDS

BACKGROUND OF THE INVENTION

The present invention relates to an improved prophylactic sheath or condom of the type normally employed by men to prevent the transmission of venereal diseases and more particularly to pevent the release of semen into the vagina of a woman during interrcourse, An object of the invention is to provide means for preventing the spilling of semen from the open end or neck of the condom during movements occurring after ejaculation.

A further object is to prevent the sliding of the neck of the condom on the skin of the penis and the untimely slipping of the condom from the penis due to the lubrication resulting from the forcing of the seminal fluid along the surface of the penis under the condom wall by movements occurring during and after ejaculation, A further object is to prevent or reduce the likelihood of rupturing the condom as sometimes occurs after ejaculation when the relatively dryer external lips of the vagina resists reentry while the male organ, lubricated with semen or precoital fluid, slides freely inside the condom thereby stretching it beyond its elastic limit on a subsequent deep penetration.

It is well known that the thin rubber tubular sheath type of condom occasionally ruptures during coitus. This usually happens during the height of coital movement after ejaculation. The reason for rupture according to some current advertising literature has been attributed to the stretching of the rubber material due to the added volume of the seminal fluid issued from penis. New shapes of such prophylactics now being sold are formed with a small reservoir at the forward end advertised to receive fluid without stretching the condom member itself. These forms with the reservoir are no less likely to rupture than the more conventional form with the simple rounded end, and in fact, under the usual conditions existing after ejaculation the reservoir design is the more likely to rupture. The reasons for this seeming paradox are simple.

The conventional rubber condom has an elastic limit orders of magnitude greater than needed to accommodate the increased volume of the ejaculated semen. If this were not so, one size of condom would not be as universally usable as it is, since the variation in the size of the erect human penis is far greater than the 2 to 5 cc of semen normally issued during ejaculation. As a demonstration it can be shown that such a condom may be stretched repeatedly from a relaxed length near 7½ inches to a length of 48 inches without damage. Further, it may be blown up with air to a size of 8 inches in diameter and over 30 inches long and relaxed repeatedly without rupture. Therefore it is not the small increase in volume due to semen that contributes to the rupture of a condom after ejaculation.

After the emission of semen the pressure of the forward walls of the vagina against the condom transports the semen along the penis toward the open end of the condom and thereby lubricates the penis so that the condom slips more freely on the penis than against the walls of the vagina. This is especially true if the penis is withdrawn totally or to such an extent that the lubricated portion of the penis extends outside the relatively dryer lips of the vagina. The movement of the condom into the vagina is further inhibited occasionally by resistance against pubic hair. During a subsequent deep penetration of the penis, the closed end of the condom can be stretched beyond its elastic limit. A normal thrust can easily exceed the few pounds of force needed to push through and rupture the thin wall of the rubber membrane. The cutting action of the pubic hair may increase the tendency to rupture.

A condom designed to have a small reservoir at the forward end, ostensibly for receiving and holding semen, does not eliminate the action just described and inherently increases the tendency to rupture under that action because the glans of the penis is forced into the reservoir having a diameter much smaller than the penis and so tends to stretch this region more than any other part of the condom.

SUMMARY OF THE INVENTION

According to the invention, there is means defining an outer sheath in the form of a thin rubber tube closed at one end and open at the other and means defining an inner partial sheath of thin rubber open at both ends inside of said outer sheath with means between the inner and outer sheath establishing a fluid-tight seal so that the inner and outer sheaths form a fluid reservoir therebetween. According to a more specific form of the invention, the outer sheath is formed with a reenforced rim at the open end. According to a more specific embodiment of the invention, the inner and outer sheaths comprise first and second condoms with the first condom having a portion near the open end rolled inside itself and the second condom then closing the first so that the region between the first condom rim and the open end of the condom thus folded remains dry.

Numerous other features, objects and advantages of the invention will become apparent from the following specification when read in connection with the accompanying drawing in which:

BRIEF DESCRIPTION OF THE DRAWING

FIG. 2 is a longitudinal cross section through a preferred condom design according to the present invention.

FIG. 3 is a transverse cross section taken at 3—3 in

FIG. 4 is a longitudinal cross section illustrating a modification.

FIG. 5 is a longitudinal cross section illustrating another modification.

FIG. 6 is an enlargment of the closed end of the modification illustrated in FIG. 5.

FIGS. 7–9 each show a longitudinal cross section of still other modifications of the invention.

DETAILED DESCRIPTION OF PREFERRED EMBODIMENTS

Figure 1A:
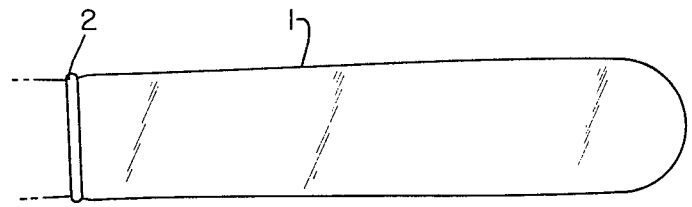
FIGS. 1A–1E show steps in applying a condom in a novel way.
Figure 1B:
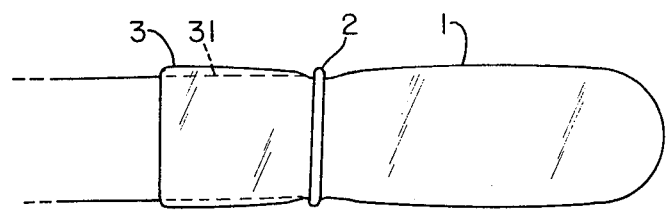
Figure 1C:
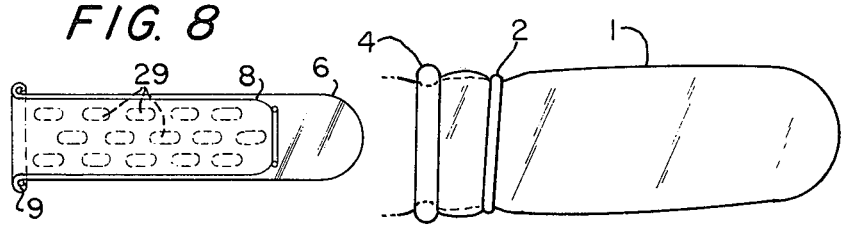
Figure 1D:
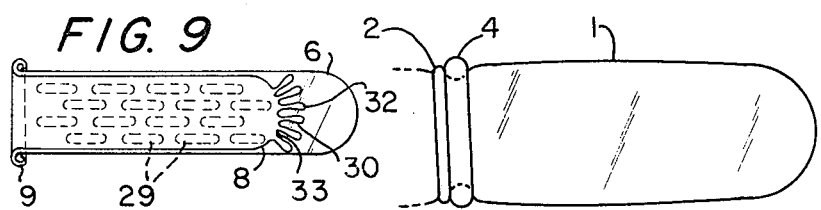
Figure 1E:
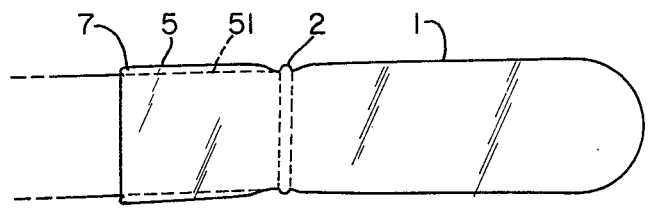
Figure 1F:
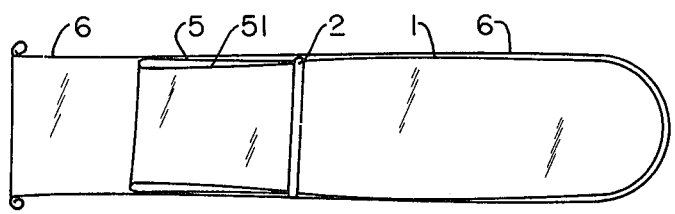
FIG. 1F is a longitudinal cross section through a pair of conventional condoms with one applied in said novel way so as to prevent the escape of semen as hereinafter described.

I have found that the use of two condoms applied and worn as indicated in FIGS. 1A–1F redues the problem of slipping and rupture and virtually eliminates the problem of spilling. The first condom is applied in the conventional way as shown in FIG. 1A by unrolling to its full length. The reinforced rim 2 is then stretched and folded back 2 to 3 inches as shown in FIG. 1B so as to make a double layer 1 to 1½ inches wide. This double layer 3 and 31 is rolled away from the base of the penis as shown in FIG. 1C to form a roll 4 at the position of the reinforced rim 2 of the condom 1; the rim 2 is then stretched slightly and pulled back over the roll 4, and allowed to relax against the penis as shown in FIG. 1D; the roll 4 is then unrolled toward the base of the penis so as to form a double layer 5 and 51 similar to 3 and 31, but now with the reinforced end of the prophylactic covered by the main tubular section 1 as shown in FIG. 1E. The second condom 6 is next applied in the usual way and unrolled completely as indicated schematically in the sectional view of FIG. 1F. With this arrangement, the second condom will be in contact with an inch or more of the dry skin at the base of the penis. Semen will be prevented from reaching this area, because the turned under portion 51 of the first condom 1 forms a cul-de-sac 7 which prevents the further progress of the semen regardless of subsequent coital activity. The semen cannot get under the under-turned portion of the first condom because the reinforced edge 2 holds it tightly against the penis and the fluid simply passes over it and presses it more firmly against the penis.

During coitus, if the penis is not withdrawn too far, the 1 inch or so of contact between the second prophylactic and the penis has sufficient friction to hold both condoms in position. The double strength of the two membranes over the glans further aids in preventing rupture.

The present invention is intended to provide in a single condom the advantages of the use of the two condoms arrangement as herebefore described. Said invention reduces the tendency to slip or slide off, reduces the possibility of rupture, substantially eliminates the problem of spilling and increases the sensitivity the male organ by having only a single layer of rubber membrane over the glans.

The present invention as illustrated in FIGS. 2-6 comprises an outer sheath member, similar to the customary single layered condom 6, supplemented by an inner partial sheath 8 that joins with the outer sheath and forms a liquid-tight seal at the reinforced outer edge 9. Said inner partial sheath is bonded to the outer sheath, by means commonly known to those familiar with the art, along a plurality of axially oriented narrow bands extending from positions near the reinforced edge 9 to within approximately ⅛ inch from the free end 10 of the inner sheath as indicated by dotted lines 11 in FIG. 2 and as further indicated by the joined portions 11 shown in the transverse cross section of FIG. 3. Between the narrow bands along which the two sheaths are joined, there are pockets 12 which form small reservoirs that in combination form a cul-de-sac for semen and/or precoital fluid. The semen is prevented from touching the penis beyond the edge 10 of the inner sheath. There is little danger of breaking these pockets because the greatest pressure that will normally be exerted on the fluid is that produced by the muscles of the vagina which generally are not strong enough to cause a pressure that would rupture the rubber membrane.

FIG. 4 shows a modified embodiment of this invention in which the inner sheath extends nearly to the position occupied by the glans and has a lightly reinforced edge 13 that has a smaller diameter than the rest of the sheath so that when worn the reinforced edge will lie behind the glans and press against this area of the penis with slightly more pressure than the rest of the sheath thereby producing a more certain barrier to the seepage of semen under the inner sheath.

The increased length of the inner sheath permits greater withdrawal of the penis during coitus without danger of the outer sheath being restricted in its inward movement by the relatively dryer exterior parts of the pudendum after the issuance of either precoital fluid or semen or both.

The bonded strips 11 shown in FIG. 4 are terminated at 14, a small distance (for example ¼ to ½ inch) before reaching the reinforced rim or edge at which the inner and outer sheaths are sealed together; this allows for an equalization of pressure in the pockets 12 and the reduction or limitation of pressure that might be developed in one or a few pockets during some motions as for example when the male organ is pressed hard against the bridge of the pelvis during a penetrating thrust.

A further modification in which the inner partial sheath 15 is smaller and is attached to the wall of the outer sheath near the closed end is shown in FIGS. 5 and 6. The inner sheath is bonded along a band 16 at the end of the inner sheath and the inner sheath is then folded back (so as to minimize stress concentration resulting from fluid pressure along the seam) toward the closed end of the outer sheath and bonded at a suitable number of locations 17. The inner sheath is preferably provided with a lightly reinforced edge 18 to fit securely behind the glans when worn properly. By this means the fluids are retained near the forward end of the penis which can be kept completely within the vagina even during the height of activity after emission of any fluid from the male organ. This modification has the advantage of using less rubber, providing greater sensitivity along the shaft of the penis because of the single layer of rubber over most of that area, and eliminating the problem of developing large pressures by movement of the penis when pressed hard against the bony bridge of the pelvis. The usual care will be needed in inserting the penis into the vagina at any time after any fluid has been emitted by the penis. This is the same care needed for insertion when using any conventional condom of the thin rubber membrane type when the glans is moist and the pudendum is not thoroughly lubricated.

FIG. 7 shows a modification of the form illustrated in FIGS. 5 and 6 in which for increased strength the inner sheath 19 is a folded-under continuation of the outer sheath 20 that is designed to cover and enclose the end of the penis. Said inner sheath 19 is held in place by bonding at a plurality of patches 21 thereby providing a plurality of passages 22 therebetween for the passage of fluid into the cul-de-sac region 23 where it is stopped in its backward flow. The inner sheath 19 is shown as having a leading feather edge 24 substantially smaller in diameter than the outer sheath so that said feather edge 24 will cling tightly to the penis and with a minimum of pressure against the penis prevent seepage of fluid under the inner sheath 19.

The combined inner and outer sheaths 19 and 20 are held in place on the penis by an extension sheath 25 that may be formed directly as part of the assembly during the original formation of the rubber membranes or may be formed as a tube open at both ends, reinforced at the rear end 26 and tapered gradually at the forward end 27 over a region 28 that is ¼ to ½ of an inch long more or less; at said region 28 the inside surface of said extension sheath 25 is bonded to the rearward outside surface of said outer sheath 20.

FIG. 8 shows a modification of the form illustrated in FIG. 4 in which the longitudinal bonded strips 11 are replaced by a number of smaller banded areas 29 located more or less uniformly so as to distribute the resistive force from the outer sheath to the inner sheath without causing force concentrations that might result in rupture of the membrane at one or more edges of the bonded areas.

FIG. 9 shows a modification of the form shown in FIG. 1 in which the inner edge of the innermost sheath, which has been described above and illustrated as being slightly smaller in diameter than the outer sheath to effect a good seal either slightly reinforced to aid that seal or tapered in thickness to a feather edge for greater comfort, may have a plurality of narrow, thin pigtails 30 extending substantially axially toward the closed end of the outer sheath and bonded at their extremities 32 to the outer sheath 6 as a means for properly and automatically controlling the position of said edge 33 of the inner sheath when the condom is unrolled in application.

There has been described novel apparatus and techniques for preventing undesired fluid leakage from condoms with apparatus that is relatively easy and inexpensive to manufacture and use while preserving virtually all the essential functions of conventional condoms. It is evident that those skilled in the art may now make numerous uses of and departures from the specific embodiment described herein without departing from the inventive concepts. Consequently, the invention is to be construed as limited only by the spirit and scope of the appended claims.

What is claimed is:

1. Prophylactic apparatus comprising,
    means defining an outer sheath in the form of a thin rubber tube closed at one end and open at the other and an inner sheath of thin rubber open at both ends,
    and means for establishing liquid sealing relationship between said inner and outer sheaths near the open end of said outer sheath to form at least a double wall near said open end with the region between defining a reservoir for retaining fluids originating between the inner opening of said inner sheath and the closed end of said outer sheath while the region on the inside of said inner sheath remains essentially dry,
    said inner sheath inside said outer sheath being secured to said outer sheath at a plurality of locations to form a double wall with means for receiving and limiting the travel of fluids produced inside said apparatus.

2. Prophylactic apparatus in accordance with claim 1 wherein said inner sheath extends inside said outer sheath for a short distance of between substantially 1 and 5 inches.

3. Prophylactic apparatus in accordance with claim 1 wherein said inner sheath extends inside said outer sheath so that the innermost edge of the inner sheath rests against the penis closely behind the edge of the glans.

4. Prophylactic apparatus in accordance with claim 1 wherein said inner sheath is shorter than said outer sheath and bonded thereto along a narrow circumferential band of the order of 2 to 5 inches from the outer sheath closed end and extends for of the order of between 1 and 4 inches over part of which distance the inner and outer sheaths are bonded together along a plurality of narrow axial bands extending from positions near said circumferential band to positions adjacent the innermost edge of the inner sheath.

5. Prophylactic apparatus in accordance with claim 1 wherein the innermost part of the inner sheath tapers to a diameter at its innermost edge that is significantly smaller than the diameter of the outer sheath for firmly engaging the penis directly behind the glans.

6. Prophylactic apparatus in accordance with claim 1 wherein the innermost edge of the inner sheath is lightly reinforced.

7. Prophylactic apparatus in accordance with claim 1 wherein the innermost edge of the inner sheath has a feather edge.

8. Prophylactic apparatus in accordance with claim 1 wherein said apparatus is made of one piece of rubber.

9. Prophylactic apparatus in accordance with claim 8 wherein said apparatus is folded inside and under to form said inner sheath that extends toward said closed end for a distance of the order of between 2 and 6 inches.

10. Prophylactic apparatus in accordance with claim 1 wherein said inner sheath extends inside said outer sheath with the innermost edge of the inner sheath extending to within the order of 1.5 inches from the closed end of the outer sheath.

11. Prophylactic apparatus in accordance with claim 1 wherein said inner and outer sheaths are bonded together at a plurality of small bonded areas located substantially uniformly over the area extending from a location of the order of 0.5 inch from said liquid sealing relationship between said inner and outer sheath near said open end of said outer sheath to a location of the order of 0.125 inch from said inner opening of said inner sheath.

12. Prophylactic apparatus in accordance with claim 1 wherein the inner opening of said inner sheath has a plurality of narrow pigtails that extend toward said closed end of said outer sheath and at their ends are secured to said outer sheath.

* * * * *